(12) United States Patent
Houser et al.

(10) Patent No.: US 8,460,326 B2
(45) Date of Patent: *Jun. 11, 2013

(54) ULTRASONIC SURGICAL SHEARS AND METHOD FOR SEALING A BLOOD VESSEL USING SAME

(75) Inventors: Kevin L. Houser, Springboro, OH (US); Sarah A. Noschang, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/462,946

(22) Filed: May 3, 2012

(65) Prior Publication Data

US 2012/0215244 A1 Aug. 23, 2012

Related U.S. Application Data

(63) Continuation of application No. 11/065,671, filed on Feb. 24, 2005, now Pat. No. 8,182,501.

(60) Provisional application No. 60/548,308, filed on Feb. 27, 2004.

(51) Int. Cl.
*A61B 17/32* (2006.01)

(52) U.S. Cl.
USPC .......................................................... 606/169

(58) Field of Classification Search
USPC ............................ 606/169, 205–208; 604/22
See application file for complete search history.

(56) References Cited

U.S. PATENT DOCUMENTS

| | | | |
|---|---|---|---|
| 5,322,055 A | 6/1994 | Davison et al. | |
| 5,776,130 A | 7/1998 | Buysse et al. | |
| 5,947,984 A | 9/1999 | Whipple | |
| 6,024,750 A | 2/2000 | Mastri et al. | |
| 6,063,050 A | 5/2000 | Manna et al. | |
| 6,187,003 B1 | 2/2001 | Buysse et al. | |
| 6,254,623 B1 | 7/2001 | Haibel, Jr. et al. | |
| 6,325,811 B1 | 12/2001 | Messerly | |
| 6,352,532 B1 | 3/2002 | Kramer et al. | |
| H2037 H | 7/2002 | Yates et al. | |
| 6,458,142 B1 | 10/2002 | Faller et al. | |
| 6,669,690 B1 | 12/2003 | Okada et al. | |
| 7,156,846 B2 | 1/2007 | Dycus et al. | |
| 2002/0026184 A1 | 2/2002 | Witt et al. | |
| 2002/0120306 A1 | 8/2002 | Zhu et al. | |
| 2002/0183785 A1 | 12/2002 | Howell et al. | |
| 2003/0114874 A1 | 6/2003 | Craig et al. | |
| 2003/0120306 A1 | 6/2003 | Burbank et al. | |

FOREIGN PATENT DOCUMENTS

| | | |
|---|---|---|
| EP | 0908152 B1 | 1/2002 |
| EP | 1362555 B1 | 6/2005 |
| JP | 8-503621 T | 4/1996 |
| JP | 11-197157 A | 7/1999 |
| WO | WO 01/24713 A1 | 4/2001 |

OTHER PUBLICATIONS

McCarus, Steven D., MD; Physiologic Mechanism of the Ultrasonically Activated Scalpel; Journal of the American Ass'n of Gynecologic Laparoscopists; Aug. 1996; vol. 3 No. 4 p. 601ff.
International Search Report dated Oct. 5, 2009; International Application No. 05723929.5.
Feil, Wolfgang, MD et al.; Ultrasonic Energy for Cutting, Coagulating, and Dissecting; p. IV, 17, 21, 23; ISBN 3-13-127521-9 (New York, NY, Thieme New York, 2005).
Emam, Tarek et al., "How Safe is High-Power Ultrasonic Dissection?," Annals of Surgery 2003, 186-191 pp., vol. 237, No. 2, Lippincott Williams & Wilkins, Inc. 2003, Philadelphia, PA.

*Primary Examiner* — Ryan Severson
(74) *Attorney, Agent, or Firm* — Verne E. Kreger, Jr.

(57) ABSTRACT

An ultrasonic surgical shears includes an ultrasonic surgical blade, a clamping arm operable to open and close toward the blade, and a tissue pad attached to the clamping arm. A method for sealing a blood vessel of a patient includes obtaining an ultrasonic surgical shears and positioning the blood vessel between the blade and the tissue pad. The clamping arm is operated to exert an average coaptation pressure on the blood vessel between and including 60 psi and 210 psi. The blade is ultrasonically vibrated to transect and seal the blood vessel.

23 Claims, 4 Drawing Sheets

ULTRASONIC SURGICAL SHEARS AND METHOD FOR SEALING A BLOOD VESSEL USING SAME

REFERENCE TO RELATED APPLICATIONS

The present application is a continuation of U.S. patent Ser. No. 11/065,671 filed Feb. 24, 2005, now U.S. Pat. No. 8,182,501, which claims the priority benefit of U.S. provisional patent application Ser. No. 60/548,308, filed on Feb. 27, 2004, wherein the contents of both applications are incorporated herein by reference.

This application contains subject matter related to co-owned patent application Ser. No. 10/289,787, filed on Nov. 7, 2002, entitled "Ultrasonic Clamp Coagulator Apparatus Having an Improved Clamping End-Effector", United States Pub. 2003/0114874, the contents of which is incorporated herein by reference.

FIELD OF THE INVENTION

The present invention is related generally to surgical instruments, and more particularly to an ultrasonic surgical shears and to a method for sealing a blood vessel using an ultrasonic surgical shears.

BACKGROUND OF THE INVENTION

Ultrasonic surgical instruments are known which include ultrasonic surgical shears having an ultrasonic surgical blade, a clamping arm operable to open and close toward the blade, a tissue pad attached to the clamping arm and including a 0.033 square-inch clamping surface area, and a device for exerting a 1.5 pound clamping force on the clamping arm which creates a clamping pressure of 45 psi (pounds per square inch) on a blood vessel which is positioned between the clamping surface area of the tissue pad and the blade. It is noted that the clamping surface area is the area where the blade and the tissue pad are in close proximity when the clamping arm is in a closed position. Exemplary devices are described in U.S. Pat. Nos. 5,322,055 and 6,325,811, the contents of which are incorporated herein by reference. The result of the ultrasonically-vibrating ultrasonic surgical blade and the clamping pressure on the blood vessel is a coaptation of the blood vessel (a bringing together of the walls of the blood vessel), a transection (a cutting) of the coaptated blood vessel, and a coagulation (a sealing) of the coaptated cut ends of the blood vessel. It is known that blood-vessel transection times can be decreased with the application of a higher clamping force. However, this is not done because conventional thought is that decreasing the blood-vessel transection time using a higher clamping force will lead to a degradation in coagulation performance (i.e., a lowering of the burst pressure of a sealed end of the transected blood vessel). Conventional ultrasonic surgical shears are not used on blood vessels larger than 3 mm because the clamping force used is inadequate for proper coaptation.

Still, there is a need in the medical device industry for improved ultrasonic surgical shears and improved methods for sealing a blood vessel using an ultrasonic surgical shears.

SUMMARY OF THE INVENTION

A first method of the invention is for sealing a blood vessel of a patient and includes steps a) through d). Step a) includes obtaining an ultrasonic surgical shears including an ultrasonic surgical blade, a clamping arm operable to open and close toward the blade, and a tissue pad attached to the clamping arm. Step b) includes positioning the blood vessel between the blade and the tissue pad. Step c) includes operating the clamping arm to exert an average coaptation pressure on the blood vessel between and including 60 psi and 210 psi. Step d) includes ultrasonically vibrating the blade to transect and seal the blood vessel.

A first embodiment of the invention is for an ultrasonic surgical shears including an ultrasonic surgical blade, a clamping arm, and a tissue pad. The clamping arm is operable to open and close toward the blade. The tissue pad is attached to the clamping arm. The ultrasonic surgical shears also includes a device for exerting a clamping force on the clamping arm creating an average clamping pressure between and including 60 psi and 210 psi on tissue positioned between the tissue pad and the blade.

A second embodiment of the invention is for an ultrasonic surgical shears including an ultrasonic surgical blade, a clamping arm, and a tissue pad. The clamping arm is operable to open and close toward the blade. The tissue pad is attached to the clamping arm. The ultrasonic surgical shears also includes a mechanism for limiting a user-applied clamping force on the clamping arm creating an average clamping pressure between and including 60 psi and 210 psi on tissue positioned between the tissue pad and the blade.

Several benefits and advantages are obtained from one or more of the method and the embodiments of the invention. Exerting an ultrasonic surgical shears coaptation pressure from 60 psi to 210 psi provides for improved blood vessel sealing with shorter transection times on 3 mm or smaller blood vessels than conventionally is possible and provides for blood vessel sealing with acceptable transection times and burst pressures on blood vessels larger than 3 mm, which is not conventionally possible.

Applicants experimentally found that applying an ultrasonic surgical shears coaptation pressure ranging from 60 psi to 210 psi (corresponding to a fully-engaged clamping surface area of 0.033 square inches and a clamping force ranging from 2 to 7 pounds) on 4.5 mm to 5 mm diameter blood vessels resulted in successful blood-vessel sealing with transection times of 2 to 4 seconds and with burst pressures of generally 500 to 700 mmHg compared to a transaction time of over 9 seconds and a burst pressure of generally 100 mmHg for a 45 psi clamping pressure (corresponding to a fully-engaged clamping surface area of 0.033 square inches and a clamping force of 1.5 pounds). Applicants also experimentally found that applying an ultrasonic surgical shears coaptation pressure ranging from 120 psi to 180 psi (corresponding to a fully-engaged clamping surface area of 0.033 square inches and a clamping force ranging from 4 to 6 pounds) on 5 mm to 7 mm diameter blood vessels resulted in successful blood-vessel sealing with transection times of 1.5 to 2.0 seconds and with burst pressures of generally 500 mmHg compared to a transaction time of generally 4.5 seconds and a burst pressure of generally 30 mmHg for a 45 psi clamping pressure (corresponding to a fully-engaged clamping surface area of 0.033 square inches and a clamping force of 1.5 pounds).

The present invention has, without limitation, application with straight or curved ultrasonic surgical blades as disclosed in the patents incorporated by reference for use in open or endoscopic procedures as well as in robotic-assisted instruments.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is understood that any one or more of the following-described embodiments, examples, etc. can be combined with any one or more of the other following-described embodiments, examples, etc.

Figure 1:
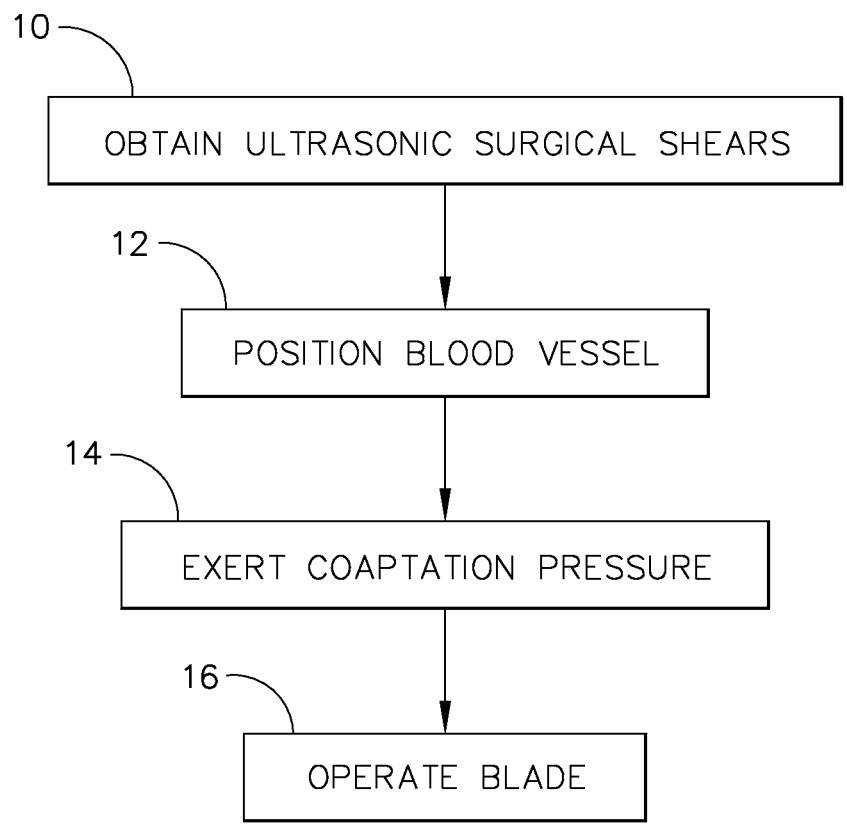
FIG. 1 is a block diagram of a method of the invention.

Referring now to the Figures, in which like numerals indicate like elements, FIG. 1 illustrates a method of the invention. The method is for sealing a blood vessel of a patient and includes steps a) through d). Step a) is labeled as "Obtain Ultrasonic Surgical Shears" in block 10 of FIG. 1. Step a) includes obtaining an ultrasonic surgical shears including an ultrasonic surgical blade, a clamping arm operable to open and close toward the blade, and a tissue pad attached to the clamping arm. Step b) is labeled as "Position Blood Vessel" in block 12 of FIG. 1. Step b) includes disposing the blood vessel between the blade and the tissue pad. Step c) is labeled as "Exert Coaptation Pressure" in block 14 of FIG. 1. Step c) includes operating the clamping arm to exert an average coaptation pressure on the blood vessel between and including 60 psi and 210 psi. Step d) is labeled as "Operate Blade" in block 16 of FIG. 1. Step d) includes ultrasonically vibrating the blade to transect and seal the blood vessel.

In one illustration of the method of the invention, step b) includes positioning the blade and the clamping arm with the blade and the tissue pad surrounding the blood vessel so that the blood vessel is disposed between the blade and the tissue pad.

In one application of the method of the invention, the average coaptation pressure in step c) is between and including 120 psi and 180 psi. In one variation, the average coaptation pressure in step c) is substantially 150 psi. In one example of the method, the blood vessel has an outside diameter greater than substantially 3 mm. In one variation, the blood vessel has an outside diameter between and including 4.5 mm and 5.0 mm. In another variation, the blood vessel has an outside diameter between and including 5.0 mm and 7.0 mm. In another example, the blood vessel has an outside diameter less than or equal to substantially 3 mm.

Figure 4:
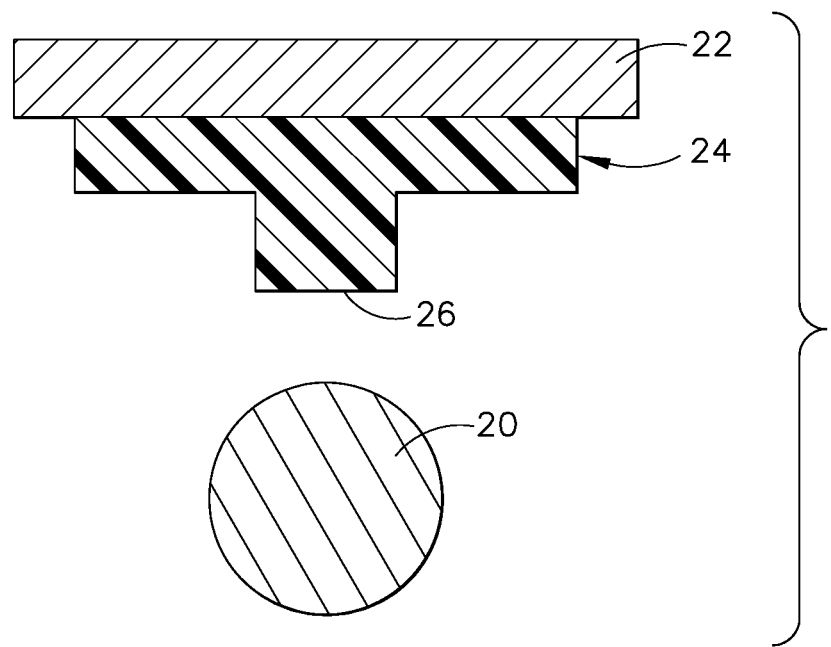
FIG. 4 is a cross sectional view of the ultrasonic surgical shears of FIG. 2, taken along lines 4-4 of FIG. 2.
Figure 5:
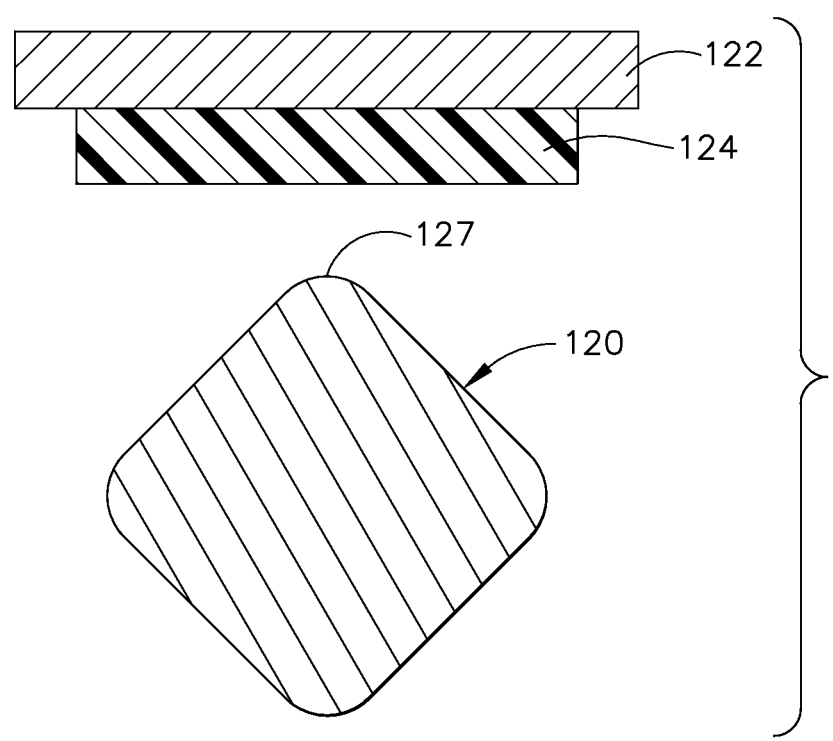
FIG. 5 is a view, as in FIG. 4, but of a different construction of the ultrasonic surgical shears of FIG. 2.

In one exemplary construction employing the method of the invention, as shown in FIG. 4, the blade 20 has a portion which opposes the tissue pad 24 and which has a substantially round transverse cross section, and the tissue pad 24, which is attached to the clamping arm 22, has a substantially "T" shape transverse cross section with the bottom of the "T" defining a clamping surface area 26, the clamping surface area 26 faces substantially toward the blade 20, and step b) disposes the blood vessel between the blade 20 and the clamping surface area 26. In a different construction, as shown in FIG. 5, the blade 120 has a portion which opposes the tissue pad 124 and which has a substantially square transverse cross section with a rounded edge defining a clamping surface area 127, the tissue pad 124, which is attached to the clamping arm 122, has a substantially rectangular transverse cross section, the clamping surface area 127 of the blade 120 faces substantially toward the tissue pad 124, and step b) disposes the blood vessel between the clamping surface area 127 and the tissue pad 124. Other blades, known to those skilled in the art, are equally useful to practice this invention.

In one implementation of the method of the invention, the tissue pad has a clamping surface area of substantially 0.033 square inches. In one variation, step c) exerts a clamping force on the clamping arm between and including 2 pounds and 7 pounds. It is noted that pressure is force per unit area, and that for the same force applied by the clamping arm, the pressure on the engaged portion of a blood vessel that fully engages the entire clamping surface area is less than the pressure on the engaged portion of a blood vessel that, because of smaller diameter, engages only a fraction of the clamping surface area. The pressures discussed herein are pressures seen by tissue when the entire clamping surface area is in contact with the tissue. As previously mentioned, a clamping surface area is the area where the blade and the tissue pad are in close proximity when the clamping arm is in a closed position.

Figure 2:
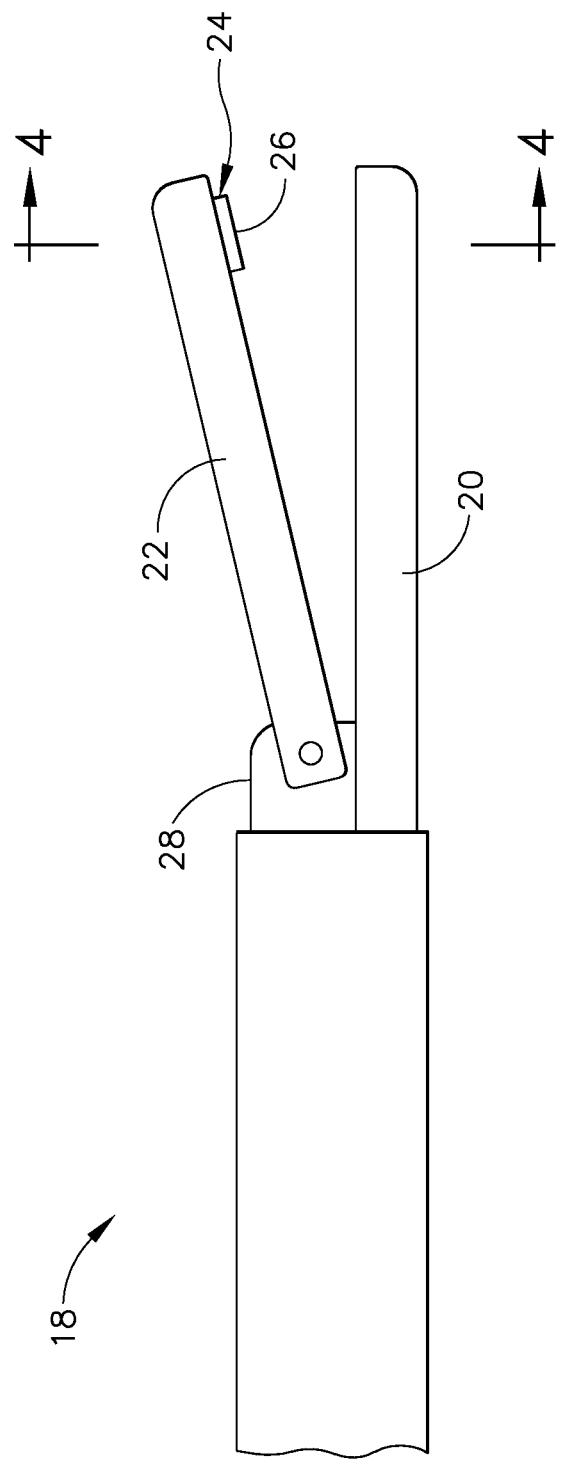
FIG. 2 is a schematic side elevational view of a portion of a first embodiment of an ultrasonic surgical shears of the invention which, in one application, is used to perform the method of FIG. 1.

A first embodiment of the invention is for an ultrasonic surgical shears 18 and is shown in FIG. 2. The ultrasonic surgical shears 18 includes an ultrasonic surgical blade 20, a clamping arm 22, and a tissue pad 24. The clamping arm 22 is operable to open and close toward the blade 20. The tissue pad 24 is attached to the clamping arm 22. The ultrasonic surgical shears 18 also includes means 28 for exerting a clamping force on the clamping arm 22 creating a clamping pressure between and including 60 psi and 210 psi on tissue disposed between the tissue pad 24 and the blade 20.

In one enablement of the first embodiment of FIG. 2, the clamping-force-creating means 28 includes a motor which rotates one of the clamping arm and the blade relative to the other of the clamping arm and the blade, wherein the motor is preselected to cause a known-size clamping surface area to exert the desired pressure on tissue large enough to cover the clamping surface area. In another enablement, the clamping-force-creating means 28 includes user-settings to set the value or range of the force or pressure, such settings operating to select a voltage or current to control a variable torque motor to cause a known-size clamping surface to exert the desired pressure or a pressure within a range of desired pressures. In a further enablement, the clamping-force-creating means 28 includes a substantially constant force spring, which applies a predetermined force to the clamping arm. In one variation, the spring is torsional in its application of force. In another variation, the spring is axial in its application of force. It is noted that U.S. Pat. No. 6,325,811 describes one embodiment of a constant force spring design. Other equivalent enablements are left to the artisan.

In one application of the first embodiment of FIG. 2, the clamping pressure is between and including 120 psi and 180 psi. In one variation, the clamping pressure is substantially 150 psi. In one implementation of the first embodiment of FIG. 2, the tissue pad 24 has a clamping surface area 26 of substantially 0.033 square inches. In one variation of this implementation, the clamping force on the clamping arm 22 is between and including 2 pounds and 7 pounds.

Figure 3:
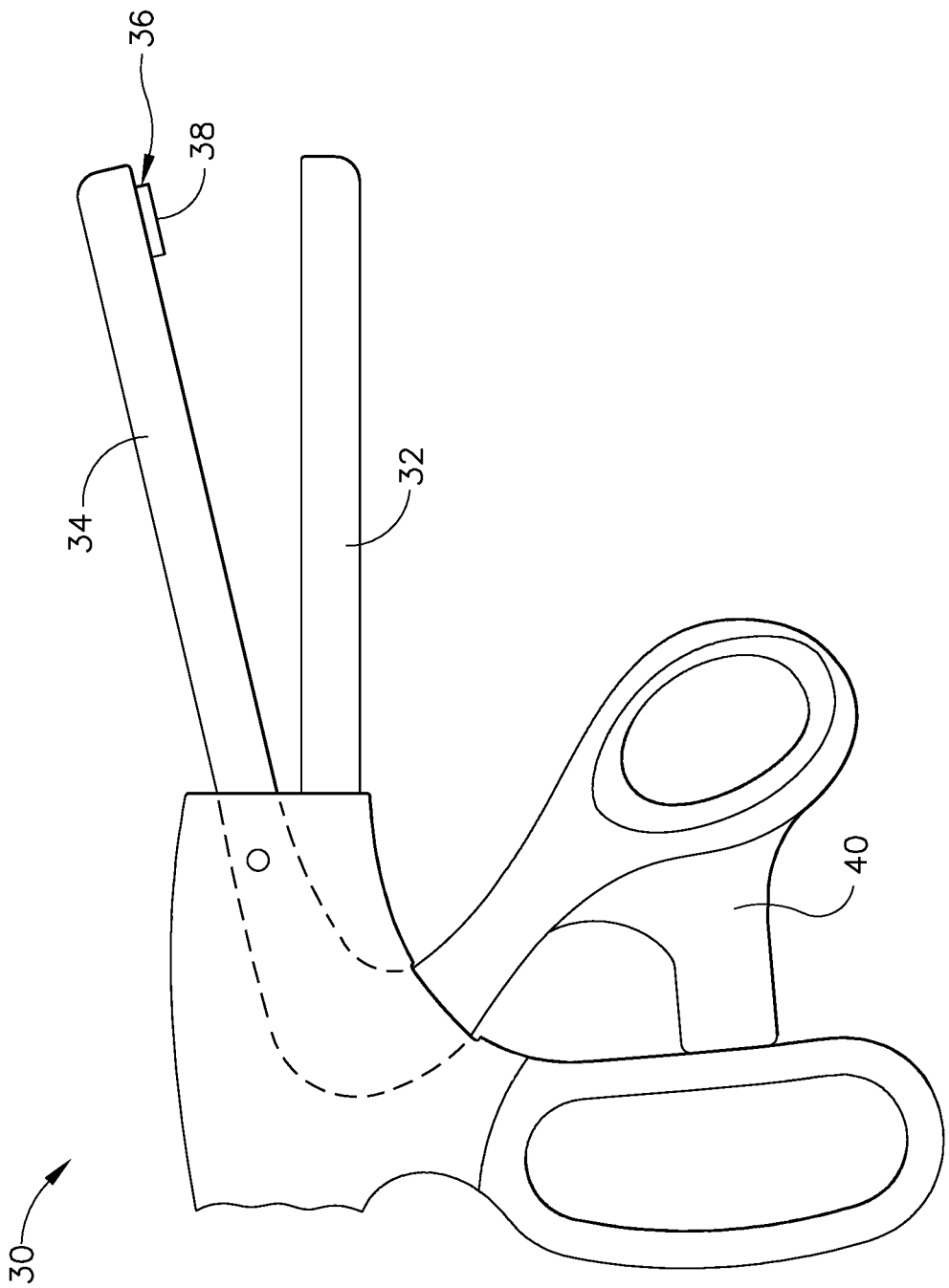
FIG. 3 is a schematic side elevational view of a portion of a second embodiment of an ultrasonic surgical shears of the invention.

A second embodiment of the invention is for an ultrasonic surgical shears 30 and is shown in FIG. 3. The ultrasonic surgical shears 30 includes an ultrasonic surgical blade 32, a clamping arm 34, and a tissue pad 36. The clamping arm 34 is operable to open and close toward the blade 32. The tissue pad 36 is attached to the clamping arm 34. The ultrasonic surgical shears 30 also includes means 40 for limiting a user-applied clamping force on the clamping arm 34 creating a clamping pressure between and including 60 psi and 210 psi on tissue disposed between the tissue pad 36 and the blade 32.

In one enablement of the second embodiment of FIG. 3, the force-limitation means 40 includes a torque-limiting mechanism as in a conventional torque wrench. Other equivalent enablements are left to the artisan.

In one application of the second embodiment of FIG. 3, the clamping pressure is between and including 120 psi and 180 psi. In one variation, the clamping pressure is substantially 150 psi. In one implementation of the second embodiment of FIG. 3, the tissue pad 36 has a clamping surface area 38 of substantially 0.033 square inches. In one variation of this implementation, the clamping force on the clamping arm is between and including 2 pounds and 7 pounds.

Other embodiments of ultrasonic surgical shears (not shown) which can be used in the method of the invention include, without limitation, those which include a force and/or pressure sensor and a user-sensed indication of the user-applied force and/or pressure measured by the force and/or pressure sensor allowing the user to control the force or pressure. User-sensed indications include, without limitation, a visually-observed value or range on a gauge, a visually-observed value or range on a computer monitor display, a visually observed color or colors, an audibly heard signal or communication, a tactily-felt vibration, etc.

Several benefits and advantages are obtained from one or more of the method and the embodiments of the invention. Exerting an ultrasonic surgical shears coaptation pressure from 60 psi to 210 psi provides for improved blood vessel sealing with shorter transection times on 3 mm or smaller blood vessels than conventionally is possible and provides for blood vessel sealing with acceptable transection times and burst pressures on blood vessels larger than 3 mm, which is not conventionally possible.

Applicants experimentally found that applying an ultrasonic surgical shears coaptation pressure ranging from 60 psi to 210 psi (corresponding to a fully-engaged clamping surface area of 0.033 square inches and a clamping force ranging from 2 to 7 pounds) on 4.5 mm to 5 mm diameter blood vessels resulted in successful blood-vessel sealing with transection times of 2 to 4 seconds and with burst pressures of generally 500 to 700 mmHg compared to a transaction time of over 9 seconds and a burst pressure of generally 100 mmHg for a 45 psi clamping pressure (corresponding to a fully-engaged clamping surface area of 0.033 square inches and a clamping force of 1.5 pounds). Applicants also experimentally found that applying an ultrasonic surgical shears coaptation pressure ranging from 120 psi to 180 psi (corresponding to a fully-engaged clamping surface area of 0.033 square inches and a clamping force ranging from 4 to 6 pounds) on 5 mm to 7 mm diameter blood vessels resulted in successful blood-vessel sealing with transection times of 1.5 to 2.0 seconds and with burst pressures of generally 500 mmHg compared to a transaction time of generally 4.5 seconds and a burst pressure of generally 30 mmHg for a 45 psi clamping pressure (corresponding to a fully-engaged clamping surface area of 0.033 square inches and a clamping force of 1.5 pounds).

While the present invention has been illustrated by a description of several embodiments and a method, it is not the intention of the applicants to restrict or limit the spirit and scope of the appended claims to such detail. Numerous other variations, changes, and substitutions will occur to those skilled in the art without departing from the scope of the invention. For instance, the ultrasonic surgical shears and the method for sealing a blood vessel of the invention have application in robotic assisted surgery taking into account the obvious modifications of such systems, components and methods to be compatible with such a robotic system. It will be understood that the foregoing description is provided by way of example, and that other modifications may occur to those skilled in the art without departing from the scope and spirit of the appended Claims.

What is claimed is:

1. A method for sealing a blood vessel of a patient comprising the steps of:
    a) obtaining an ultrasonic surgical shears including an ultrasonic surgical blade, a clamping arm operable to open and close toward the blade, a tissue pad attached to the clamping arm, means for providing a clamp force wherein the blade and tissue pad define a clamping surface area so that the applied clamp force does not exceed a clamping pressure of 210 psi at the clamping surface area;
    b) disposing the blood vessel between the blade and the tissue pad;
    c) operating the clamping arm to exert a predetermined average coaptation pressure on the blood vessel between and including 60 psi and 210 psi; and
    d) ultrasonically vibrating the blade to transect and seal the blood vessel.

2. The method of claim 1, wherein the average coaptation pressure in step c) is between and including 120 psi and 180 psi.

3. The method of claim 2, wherein the average coaptation pressure in step c) is substantially 150 psi.

4. The method of claim 1, wherein the blood vessel has an outside diameter larger than substantially 3 mm.

5. The method of claim 4, wherein the blood vessel has an outside diameter between and including 4.5 mm and 5.0 mm.

6. The method of claim 4, wherein the blood vessel has an outside diameter between and including 5.0 mm and 7.0 mm.

7. The method of claim 1, wherein the clamping surface area is substantially 0.033 square inches.

8. The method of claim 7, wherein step c) exerts a clamping force on the clamping arm between and including 2 pounds and 7 pounds.

9. The method of claim 1, wherein the blade has a portion which opposes the tissue pad and which has a substantially square transverse cross section with a rounded edge defining a clamping surface area, wherein the tissue pad has a substantially rectangular transverse cross section, wherein the clamping surface area faces substantially toward the tissue pad, and wherein step b) disposes the blood vessel between the clamping surface area and the tissue pad.

10. The method of claim 1, wherein the means for providing a clamp force is a motor.

11. The method of claim 1, wherein the means for providing a clamp force is a spring.

12. An ultrasonic surgical shears comprising:
a) an ultrasonic surgical blade;
b) a clamping arm operable to open and close toward the blade;
c) a tissue pad attached to the clamping arm; and
d) means for exerting a predetermined clamping force on the clamping arm, wherein the blade and tissue pad define a clamping surface area so that the clamp force does not exceed a clamping pressure of 210 psi at the clamping surface area.

13. The ultrasonic surgical shears of claim 12, wherein the average clamping pressure is between and including 120 psi and 180 psi.

14. The ultrasonic surgical shears of claim 13, wherein the average clamping pressure is substantially 150 psi.

15. The ultrasonic surgical shears of claim 12, wherein the clamping surface area is substantially 0.033 square inches.

16. The ultrasonic surgical shears of claim 15, wherein the clamping force is between and including 2 pounds and 7 pounds.

17. An ultrasonic surgical shears comprising:
a) an ultrasonic surgical blade;
b) a clamping arm operable to open and close toward the blade;
c) a tissue pad attached to the clamping arm, wherein the blade and tissue pad define a clamping surface area so that the applied clamp force does not exceed a clamping pressure of 210 psi at the clamping surface area; and
d) means for creating an average predetermined clamping pressure between and including 60 psi and 210 psi on tissue disposed between the tissue pad and the blade.

18. The ultrasonic surgical shears of claim 17, wherein the average clamping pressure is between and including 120 psi and 180 psi.

19. The ultrasonic surgical shears of claim 18, wherein the average clamping pressure is substantially 150 psi.

20. The ultrasonic surgical shears of claim 17, wherein the clamping surface area is substantially 0.033 square inches.

21. The ultrasonic surgical shears of claim 20, wherein the clamping force is between and including 2 pounds and 7 pounds.

22. A method for sealing a blood vessel of a patient comprising the steps of:
a) obtaining an ultrasonic surgical shears including an ultrasonic surgical blade, a clamping arm operable to open and close toward the blade, and a tissue pad attached to the clamping arm, wherein the blade and tissue pad define a clamping surface area so that the applied clamp force does not exceed a predetermined clamping pressure of 210 psi at the clamping surface area;
b) disposing the blood vessel between the blade and the tissue pad;
c) limiting the clamping arm by means of a spring to exert between and including 60 psi and 210 psi on the blood vessel; and
d) ultrasonically vibrating the blade to transect and seal the blood vessel.

23. A method for sealing a blood vessel of a patient comprising the steps of:
a) obtaining an ultrasonic surgical shears including an ultrasonic surgical blade, a clamping arm operable to open and close toward the blade, and a tissue pad attached to the clamping arm, wherein the blade and tissue pad define a predetermined clamping surface area so that the applied clamp force does not exceed a clamping pressure of 210 psi at the clamping surface area;
b) disposing the blood vessel between the blade and the tissue pad;
c) limiting the clamping arm by means of a spring to exert between and including 60 psi and 210 psi on the blood vessel; and
d) ultrasonically vibrating the blade to transect and seal the blood vessel for no more than 4.5 secs.

* * * * *